(12) United States Patent
Reja et al.

(10) Patent No.: US 8,271,205 B2
(45) Date of Patent: Sep. 18, 2012

(54) METHOD AND SYSTEM FOR ANALYSIS OF MELT CURVES, PARTICULARLY DSDNA AND PROTEIN MELT CURVES

(75) Inventors: Valin Reja, Queens Park (AU); Alister Kwok, Sefton (AU); Glenn Stone, Glenwood (AU)

(73) Assignee: Corbett Research Pty Ltd, Wales (AU)

( * ) Notice: Subject to any disclaimer, the term of this patent is extended or adjusted under 35 U.S.C. 154(b) by 424 days.

(21) Appl. No.: 12/432,253

(22) Filed: Apr. 29, 2009

(65) Prior Publication Data

US 2010/0076690 A1    Mar. 25, 2010

(30) Foreign Application Priority Data

Sep. 19, 2008    (AU) ................................ 2008904882

(51) Int. Cl.
  *G06F 19/00*    (2011.01)
  *G06F 15/00*    (2006.01)
  *G01N 33/48*    (2006.01)
(52) U.S. Cl. ................................. 702/19; 700/1; 702/27
(58) Field of Classification Search .................... None
  See application file for complete search history.

(56) References Cited

U.S. PATENT DOCUMENTS

| | | | |
|---|---|---|---|
| 6,106,777 | A | 8/2000 | Fujita et al. |
| 6,495,326 | B2 | 12/2002 | Kurane et al. |
| 2002/0123062 | A1 | 9/2002 | Wittwer |
| 2003/0104438 | A1 | 6/2003 | Eyre et al. |
| 2008/0182252 | A1 | 7/2008 | Antovich |
| 2008/0212090 | A1 | 9/2008 | Lee et al. |

FOREIGN PATENT DOCUMENTS

| | | |
|---|---|---|
| WO | 00/66777 A2 | 11/2000 |
| WO | 2005/071113 A1 | 8/2005 |
| WO | 2007/035806 A2 | 3/2007 |

OTHER PUBLICATIONS

Zhou et al. High-Resolution DNA Melting Analysis for Simultaneous Mutation Scanning and Genotyping in Solution. Clinical Chemistry vol. 51, pp. 1770-1777 (2005).*

* cited by examiner

*Primary Examiner* — John S Brusca
(74) *Attorney, Agent, or Firm* — Baker, Donelson, Bearman, Caldwell & Berkowitz, PC

(57) ABSTRACT

A computer-implemented method of analysis of melt curve data comprising the steps of: (a) parameter model fitting the melt curve data; (b) performing a principal component analysis of the melt curve data; and (c) utilizing the principal components for clustering the melt curve data into groups. Such a method allows an efficient analysis of variations in melt curve shape and position and allows to statistically quantify these variations for both supervised and unsupervised data sets. Current melt analysis methods neither allow for statistical measures of each unknown nor do they allow for the determination of unsupervised data sets (i.e., unknown number of groups present). Particularly, the method according to the invention can be advantageous for identifying a specific sequence of dsDNA in a sample after performing a polymerase chain reaction (PCR).

22 Claims, 6 Drawing Sheets

METHOD AND SYSTEM FOR ANALYSIS OF MELT CURVES, PARTICULARLY DSDNA AND PROTEIN MELT CURVES

This application claims benefit of and priority to Australian Provisional Application No. 2008904882, entitled "Method and Apparatus for Analysis of Melt Curves," filed Sep. 19, 2008, and is entitled to that filing date for priority. The specification, drawings, attachments, and complete disclosure of Australian Provisional Application No. 2008904882 are incorporated herein in their entireties by specific reference for all purposes.

FIELD OF THE INVENTION

The present invention relates to a system and related methods for identifying a specific sequence of double stranded DNA (dsDNA) in a sample after performing a polymerase chain reaction and, in particular, relates to the analysis of Melt Curve data associated there with.

BACKGROUND OF THE INVENTION

The identification of a specific sequence of double stranded DNA in a sample after performing a polymerase chain reaction (PCR) is often difficult. Many variables, including the test conditions, sample size and the frequency of measurements, affect the often low signal-to-noise ratio that makes data analysis difficult.

PCR is well known in the art and generally refers to an in vitro method for amplifying a specific polynucleotide template sequence. The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989), all of which are incorporated herein in their entireties for all purposes.

The use of a dye that binds with dsDNA can facilitate the identification of dsDNA in a sample because some dyes increase in fluorescence when bound to dsDNA. SYBR Green I is a well-known example of a dye with this property used to identify dsDNA in a sample. The fluorescence signal of such a dye is proportional to the total quantity of dsDNA in a sample. The use of such a dye with a melting curve enhances the ability to identify a specific sequence of dsDNA in a sample.

The melting curve measures the fluorescence of the specific sample as a function of temperature. The melting temperature of a dsDNA sequence is the temperature at which half of the dsDNA sequence dissociates into single stranded DNA. Dissociation, or denaturation, is a process by which the individual strands of the dsDNA separate into single stranded DNA (ssDNA). The combined effect that different dsDNA sequences often have different melting temperatures and the fluorescence of the dye decreases when not bound to dsDNA allows the fluorescence signal from a melting curve to be used to help determine the dsDNA sequence found in a post PCR sample.

The raw melting curve data from a PCR instrument normally consists of a set of melt curves, one for each sample. A typicality melt curve consists of a decreasing fluorescence measurement with increasing temperature, as fluorophore is quenched after being released by the separating (melting) ssDNA strands. Melting is preceded by an amplification phase, and due to this and the limits of quantification of the initial sample (and other factors), the melt curves do not all start from the same initial point.

Azbel [M. Ya Azbel, "DNA Sequencing and Melting Curve", Proc. Natl. Acad. Sci., 76(1), pp. 101-105, 1979], which is incorporated herein by specific reference, discusses the rate of melting of a single DNA domain as a function of temperature. This can be translated into an idealized melt curve for a (short) domain, which has the form of a logistic equation:

$$1/1+\exp(\lambda(T-T_0)) \qquad \text{Eqn. 1}$$

where T is temperature, $T_0$ is the temperature of maximum rate of melting, and $\lambda$ is a constant controlling the spread of melting temperature (which presumably also depends on the rate of heating).

In practice this equation does not hold. However, it is important to obtain an accurate model of the Melt Curve in order to ascertain information about the dsDNA.

Furthermore, with the advent of high resolution melting (HRM) as a tool for mutation screening and discovery, analysis techniques are being sought after to allow for enhanced automated processing of larger sample sizes. At present, HRM utilizes a standard method of melt curve normalization that is typically followed by a subtraction plot, which is generated by selecting a known control. Agglomerative, unbiased clustering on these subtraction plots is performed using average linkage of samples to the known control, generating a dendogram that is used in the calling of genotypes (see [Vandersteen J G, Bayrak-Toydemir P, Palais R A, Wittwer C T, Identifying common genetic variants by high-resolution melting, Clin. Chem, 2007; 53(7): 1191-1198]; incorporated herein by specific reference). Although the method allows for automated genotyping of unknown samples, no real statistical information is provided to suggest the likely hood of an unknown sample being of a known genotype (discriminant analysis or "supervised learning") nor does it allow for the determination of the number of alleles present, which could be useful for unknown mutation discovery (cluster analysis or "unsupervised learning").

Thus, far researchers have been able to apply HRM to applications as diverse as human leukocyte antigen (HLA) typing (see [Zhou L, Vandersteen J, Wang L, Fuller T, Taylor M, Palais B, Wittwer C T, High-resolution DNA melting curve analysis to establish HLA genotypic identity, Tissue Antigens, 2004; 64(2): 156-164]; incorporated herein by specific reference), classification of organisms (see Jeffery N, Gasser R B, Steer P A, Noormohammadi A H, Classification of Mycoplasma synoviae strains using single-strand conformation polymorphism and high-resolution melting-curve analysis of the vlhA gene single-copy region, Microbiology, 2007; 153: 2679-2688]; incorporated herein by specific reference), detection and quantification of DNA methylation (see [Wojdacz T K, Dobrovic A. Melting curve assays for DNA methylation analysis. *Methods Mol Bio.* 2009; 507: 229-240]; incorporated herein by specific reference), identification of candidate predisposition genes (see [Saitsu H, Kato M, Mizuguchi T, Hamada K, Osaka H, Tohyama J, Uruno K, Kumada S, Nishiyama K, Nishimura A, Okada I, Yoshimura Y, Hirai S, Kumada T, Hayasaka K, Fukuda A, Ogata K, Matsumoto N, De novo mutations in the gene encoding STXBP1 (MUNC18-1) cause early infantile epileptic encephalopathy, Nat Genet., 2008; 40(6): 782-788]; incorporated herein by specific reference), somatic acquired mutation ratios (see [Krypuy M, Newnham G M, Thomas D M, Conron M, Dobrovic A, High resolution melting analysis for the rapid and sensitive detection of mutations in clinical samples: KRAS codon 12 and 13 mutations in non-small cell lung cancer, BMC Cancer, 2006; 6:295]; incorporated herein by specific reference), mutation discovery (see [Krypuy M, Ahmed A A, Etemadmoghadam D, Hyland S J; Australian Ovarian Cancer Study Group, DeFazio A, Fox S B, Brenton J D, Bowtell D D, Dobrovic A, High resolution melting for mutation scanning of TP53 exons 5-8, BMC Cancer, 2007; 7: 168-181]; incorporated herein by specific reference), allelic prevalence in a population (see [Polakova K M, Lopotova T, Klamova H, Moravcova J. High-resolution melt curve analysis: initial screening for mutations in BCR-ABL kinase domain. *Leuk. Res.* 2008; 32(8): 1236-1243]; incorporated herein by specific reference), and DNA fingerprinting (see [Gale N, French D J, Howard R L, McDowell D G, Debenham P G, Brown T, Rapid typing of STRs in the human genome by HyBeacon melting, Org. Biomol. Chem, 2008; 6(24): 4553-4559]; incorporated herein by specific reference). HRM allows for the discrimination of genotypes by comparing melt curve shapes and positions relative from one sample to another following amplification of a DNA fragment containing the alleles being investigated (see [Wittwer C T, Reed G H, Grundry C N, Vandersteen J G, Pryor R J, High-resolution genotyping by amplicon melting analysis using LCGreen, Clin. Chem, 2003; 49: 853-860]; incorporated herein by specific reference). The shape and positional variation of one melt curve to another is dependent on amplicon length, guanine-cytosine (GC) content, buffer conditions and the random generation of heteroduplexes, along with other reaction variables (see [Ririe K M, Rasmussen R P, Wittwer C T, Product differentiation by analysis of DNA melting curves during the polymerase chain reaction, Analytical Biochem., 1997; 245: 154-160] or [Wittwer C T, Reed G H, Grundry C N, Vandersteen J G, Pryor R J, High-resolution genotyping by amplicon melting analysis using LCGreen, Clin. Chem., 2003; 49: 853-860]; both incorporated herein by specific reference). Heteroduplex formation allows for the detection of heterozygotes and more complex variations within a sample. For the period of cooling during the polymerase chain reaction, the re-association of denatured strands can result in mismatches between alleles of minor nucleotide variations such as single nucleotide polymorphisms (SNPs) (see [Jensen M A, Straus N, Effect of PCR conditions on the formation of heteroduplex and single-stranded DNA products in the amplification of bacterial ribosomal DNA spacer regions, PCR Methods Appl., 1993; 3: 186-194]; incorporated herein by specific reference). These mismatches will denature at lower temperatures prior to the dissociation of the matched templates, and therefore, results in a melt curve with a double inflection (see [Reed G H, Wittwer C T, Sensitivity and specificity of single-nucleotide polymorphism scanning by high-resolution melting analysis, Clin. Chem., 2004; 50(10): 1748-1754]; incorporated herein by specific reference). Homozygous variations result in a curve positional change as the amplicon with the lowest energy between nucleotide pairing and neighbouring will denature earlier, however, this method is instrument dependent, which requires a temperature uniformity of less than 0.05° C. and a temperature resolution of less than 0.1° C. (see [Liew M, Pryor R, Palais R, Meadows C, Erali M, Lyon E, Wittwer C, Genotyping of single-nucleotide polymorphisms by high-resolution melting of small amplicons, Clin. Chem., 2004; 50(7): 1156-1164] or [Herrmann M G, Durtschi J D, Bromley L K, Wittwer C T, Voelkerding K V, Amplicon DNA melting analysis for mutation scanning and genotyping: cross-platform comparison of instruments and dyes, Clin. Chem., 2006; 52(3): 494-503]; both incorporated herein by specific reference). Current HRM software packages can plot these variations in curve shape and position; however, they do not offer the ability to statistically quantify these differences for both supervised and unsupervised data sets.

Therefore, it is an object of the present invention to overcome or ameliorate at least one of the disadvantages of the prior art, or to provide a useful alternative melt curve analysis.

SUMMARY OF THE INVENTION

According to various exemplary embodiments of the present invention, this need is settled by a computer-implemented method of analysis of melt curve data as it is defined by the features of independent claim 1, by a computer-implemented system for melt curve data analysis as it is defined by independent claim 18, and by a computer-implemented method of analysis of melt curve data as it is defined by independent claim 22. Melt curve data in this context relates to melt curve data of double stranded deoxyribonucleic acid (dsDNA), of proteins or the like. Preferred embodiments of the invention are subject of the dependent claims.

In one embodiment, the invention comprises a computer-implemented method, comprising the steps of: (a) in a computer memory, parameter model fitting the melt curve data; (b) in a computer memory, performing a principal component analysis of the melt curve data; and (c) utilizing the principal components for clustering the melt curve data into groups. The method does not necessarily have to be performed in the mentioned sequence of steps. Other sequences of the step (a) to step (c) are also possible wherein the mentioned sequence is a preferred embodiment. The method according to this embodiment of the invention allows an efficient analysis of variations in melt curve shape and position and allows statistically quantifying these variations for both supervised and unsupervised data sets. Current melt analysis methods neither allow for statistical measures of each unknown nor do they allow for the determination of unsupervised data sets (i.e., unknown number of groups present). The method according to this embodiment of the invention can particularly be advantageous for identifying a specific sequence of dsDNA in a sample after performing a polymerase chain reaction (PCR).

In a preferred embodiment, step (a) comprises fitting the melt curve data to a model of the form:

$$A + \frac{B - CT}{1 + \exp(\lambda(T - T_0))}$$

where A is an estimate of the minimum observed fluorescence; B and C are estimates of the intercept and slope of the initial part of the melt curve; $T_0$ is estimated as the point of maximum (negative) slope of the melt curve, and $\lambda$ is approximately 2. With such a model for the melt curve, an efficient normalization of the actual melt curves to a more idealized and comparable form is possible.

In another preferred embodiment, step (a) comprises a scaling of the melt curve to a line of best fit. Such step (a) can prevent a loss in melt curve features that could influence the final result, post principal component extraction. Preferably, the melt curve is scaled such that a highest fluorescence value is about 100 and a lowest fluorescence value is about 0. Further, a region of melt curve data prior to the melt curve transition and a region of melt curve data following the melt curve transition are preferably selected and an average fluorescence value is preferably calculated. Preferably, no template controls are removed from the analysis. Applying such a step (a), correct calling of all the clusters and samples with high posterior probabilities and typicalities can be achieved.

In yet another embodiment, preferably at least the first two principal components are utilized in step (c). Principal component analysis allows for the determination of features within a melt curve data set. Other methods of melt curve analysis simply compare average distances between curves and therefore are incapable of statistically defining samples or detecting how many groups may be present within the data set. Preferably, said clustering occurs by means of k-means clustering or hierarchical clustering. The method of k-means clustering offers the advantage of detecting a number of groups present in a rational manner as opposed to simple determination of groups using a dendogram. K-means combined with the gap statistic allows for the determination of the true number of clusters present; dendograms can only group samples if the number of clusters is known.

Preferably, gap statistic is utilized for determining the number of groups for the melt curve data. Such a method can provide an appropriate detecting of a preferred number of clusters and principal components dimensionality. Thereby, determining the number of groups for the melt curve data preferably comprises the comparison of a measure of cluster quality to data known not to have any real clusters. In particular, the measure of cluster quality can preferably be determined applying the formula:

$$W_k = \sum_{j=1}^{k} \sum_{i \in c_j} \|x_i - \bar{x}_j\|^2$$

where $C_j$ is the j-th cluster, and $\bar{x}_j$ is its centre.

Thereby, determining the number of groups for the melt curve data preferably comprises the steps of: (i) clustering the observed data, varying the number of clusters k=1, 2, . . . , K for a maximum K and computing Wk for each k; (ii) generating B random reference data sets and clustering each as in step (i), computing Wkb for k=1, 2, . . . , K and b=1, 2, . . . , B; (iii) computing the Gap statistic and standard error for each k applying the formulae $$\text{Gap}(k) = (1/B) \sum \log(W_{kb}^*) - \log(W_k)$$

and $$s_k = \sqrt{(1 + 1/B) \sqrt{\{(1/B) \sum_b (\log(W_{kb}^*)^2 - (1/B) \sum_b \log(W_{kb}^*))^2\}}};$$

and (iv) choosing the number of clusters $\hat{k}$ to be the smallest k such that Gap(k)≧Gap(k+1)−sk+1. With respect thereto, the method does not necessarily have to be performed in the mentioned sequence of steps (i) to (iv). Other sequences of the steps (i) to (iv) are also possible wherein the mentioned sequence is a preferred embodiment.

In one embodiment, Bayes Information Criterion analysis preferably is utilized for determining the number of groups for the melt curve data. Such a method can also provide an efficient detecting of a preferred number of clusters and principal components dimensionality.

Preferably, said melt curve data is for a known substance and said clustering utilizes linear discriminant analysis (LDA) to cluster the melt curve data into groups. This can be used as an advantageous classification when the data has multivariate normal distribution and each class has the same variance/covariance matrix but different means. In particular, LDA can be an effective and efficient classifier.

Preferably, said clustering utilises a typicality index to assign the melt curve data into a group. Thus far there is no measure for how well an unknown sample belongs to a particular group. This can allow for statistical qualification of unknowns particularly in applications that may be of a diagnostic nature. Further, said melt curve and said clustering preferably utilize posterior class probabilities to cluster the melt curve data into groups. Similarly, no methods exist that allow unknowns to be qualified into which group they might belong to. As for the typicalities statistical qualification of unknown samples can have an advantage for melt curve analysis in diagnostic applications.

A further aspect of the invention deals with a computer program comprising means for performing the method described above. Herein, the term "computer program" is used synonymously with the terms "software", "program for a computer" and the like such that a computer program may correspond to any kind of computer program products. A computer program may be stored/distributed on a suitable medium, such as an optical storage medium or a solid-state medium supplied together with or as part of other hardware, but may also be distributed in other forms, such as via the Internet or other wired or wireless telecommunication systems. Such a computer program can allow its user to achieve both supervised and unsupervised genotyping of unknowns from HRM data sets in various applications of molecular biology, with the final goal being to allow for multiple run files in a diagnostic setting.

Preferably, in one embodiment the computer program comprises import means arranged to import raw high resolution melting data and parsing means arranged to syntactically analysing the imported data. With such import means an efficient and convenient further processing of recorded digitally data can be achieved. In particular, data from other software, such as, for example, raw HRM plots from the Rotor-Gene software (e.g., Rotor-Gene Q, version 1.7, Corbett Research, 2008), and, in particular, its character-delineated spread sheets, can be automatically integrated into the computer program. The import means of the computer program can also have parsing means for syntactic analysis of the data in order to ensure that correct data is processed. Furthermore, the computer program preferably comprises cropping means arranged to allow a user to avoid regions of non-specific amplification products.

In a preferred exemplary embodiment, the computer program comprises sample selection means and mode selection means arranged to allow a user to select between analysing a supervised data set or an unsupervised data set following the sample selection. This can ensure an effective normalization. Thereby, the computer program preferably comprises parameter selection means arranged to select a most appropriate cluster number and a most appropriate principal component number via k-means clustering and/or Gap statistics when the user selects analysing an unsupervised data set. Preferably, the computer program also comprises control selection means arranged to allow the user to select the appropriate controls for each genotype when the user selects analysing a supervised data set, wherein linear discriminant analysis is used and the appropriate number of principal components is determined via a cross-validation function if more than two controls are used for each group and wherein nearest neighbour classification of samples into groups which is proceeded by a re-computation using linear discriminant analysis is used if one single control activates.

In yet another embodiment, a further aspect of the invention deals with an apparatus when implementing the method described above. Preferably, such an apparatus is arranged as computer system comprising the computer program described above. With such a computer system the method according to the invention can efficiently be performed in an exact and fast manner.

BRIEF DESCRIPTION OF THE DRAWINGS

Embodiments of the invention will now be described, by way of example only, with reference to the accompanying drawings in which.

DETAILED DESCRIPTION OF EXEMPLARY EMBODIMENTS

Various exemplary embodiments of the present invention provide a method for providing improved analysis of High Resolution DNA Melt Curves (HRM), a computer program for performing the method, and a system and apparatus for implementing the method. In one exemplary embodiment, the method comprises the following steps:

melt curve parameter model fitting of HRM curves,
auto-calling of HRM curves into groups defined by known cases, and
de-novo clustering of HRM curves into groups.

The methodology disclosed can be utilized for use with a single run of an instrument. In one embodiment, it is therefore envisaged that up to 96 samples will be included. Various embodiments are also suitable to the analysis of data from multiple runs.

Figure 1:
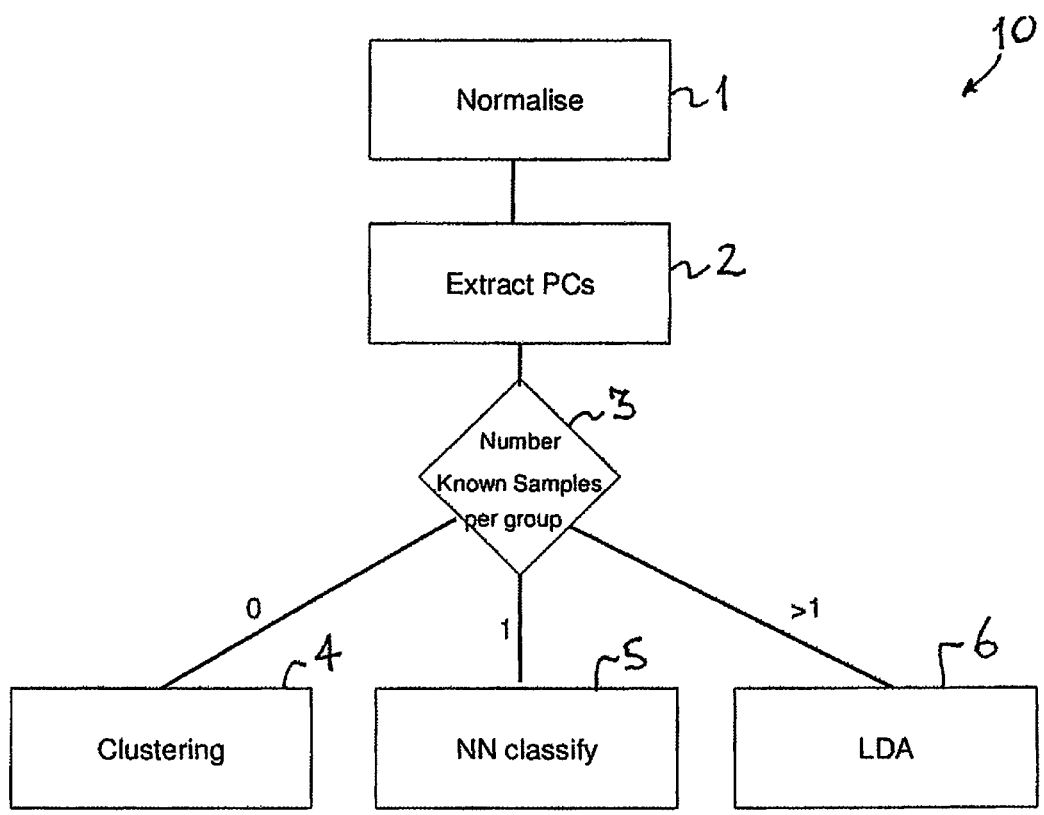
FIG. 1 shows a flow chart of the steps of an exemplary embodiment of the present invention.

Turning initially to a first exemplary embodiment of the invention, there is a flowchart of the steps 10 of the preferred embodiment shown in FIG. 1. Initially, the data is normalized 1, this is followed by a process of extracting principle components 2. Depending on the number of know samples per group 3, the data is either clustered 4, classified using a Nearest Neighbour 5 or an LDA process 6.

Acquisition of HRM Data

HRM data can be acquired with a setup using a given volume and concentration of amplicon specific oligonucleotides as reverse and forward primers, intercalating dye, reaction buffer, magnesium chloride, deoxyribonucleotides, and taq DNA polymerase. The sample can be in the form of purified DNA at a given concentration. The reaction can be cycled in order to amplify the sequence of interest, which is typically conducted using a thermal cycler (Rotor-Gene Q, Corbett Research, Aus). Following a given number of cycles the amplified sequence can be denatured using a given melt profile on the same thermal cycler with HRM capabilities (e.g. Rotor-Gene Q). During the process of the melt the temperature of the chamber can be increased over a given incrimination (typically>0.1° C.) during which time fluorescence levels of the intercalating dye are measured on the instrument. This process involves exciting the fluorescent dye using a given excitation light wavelength from a given light source (e.g. light emitting diode), which is further narrowed by the use of a given filter. The excitation light source excites the fluorescent dye which emits at a given light wavelength. The emission can be detected through a given emission filter and emission detection device (e.g. photomultiplier). Prior to the dissociation of the double stranded amplification product, the intercalating dye can be bound to the DNA and upon excitation emits at a given frequency. During the melt, the DNA product dissociates during a given temperature range which causes the intercalating dye to be released. Upon release of the dye, further excitation results in a significantly lower level of fluorescence emission. The subsequent decrease in fluorescence can be measured and plotted against temperature to generate the melt curve for each given sample. This HRM data can be acquired in digital format and stored as an electronic file. It is the electronic file of the high resolution melt that the inventive software can use to run its analysis.

Normalization 1

One main assumption underlying Eqn. 1 is that fluorescence is proportional to the amount of unmelted DNA in a temperature independent fashion. In practice, this assumption does not hold, and in addition to a degree of background, the fluorescence itself is affected by temperature.

In the preferred embodiments, a modified equation is used in a normalization process. Using a constant background A and a linear approximation to the fluorophore's inherent temperature dependence gives the following, largely empirical, model for the melt curve of a single DNA domain:

$$A + \frac{B - CT}{1 + \exp(\lambda(T - T_0))} \qquad \text{Eqn. 2}$$

Of course, in practice samples may contain mixtures (e.g.n heterozygotes) and more complex scenarios, and this would result in a more complex melt curve. However, Eqn. 2 is adequate for the purpose of normalizing the actual melt curves to a more idealized (and therefore comparable) form.

Eqn. 2 is fit to each individual melt curve by least squares using a Levenberg-Marquardt algorithm [D. W. Marquardt, "An Algorithm For Least-Squares Estimation Of Nonlinear Parameters", J. Soc. Indust. Appl. Math., 11(2), 1963], which is incorporated herein by specific reference. Least squares is equivalent to maximum likelihood for the Normal distribution; however, it is not suggested that the Normal distribution is an appropriate model for this data. In fact, it appears that the variance is somewhat dependent on the mean. For the present purposes of normalization, least squares is adequate.

The Levenberg-Marquardt algorithm is iterative and requires a reasonable set of initial values for the parameters. The following initial values can be used:

A (background) is estimated as the minimum observed fluorescence.

B and C are estimated as the intercept and slope of the initial part of the melt curve. The initial part is determined by looking for a point of maximum curvature and taking everything prior to this.

$T_0$ is estimated as the point of maximum (negative) slope of the melt curve.

$\lambda$ is initialised to be 2.

Once Eqn. 2 is fit to the melt curve for a particular sample, it might be proceeded by using just the five parameters as a summary of the curve. However, the model does not capture all of the features of the curve that are of interest, so a more empirical approach is adopted. That is, the residuals from the model are computed and added back to an idealized melt curve to produce a normalised data set.

Mathematically, suppose $\{y_T\}$ is the sequence of fluorescence values from the raw melt curve. Let $\{\hat{y}_T\}$ be the values from Eqn. 2 after fitting to the raw data. The normalized data $\{\acute{y}_T\}$ is defined by:

$$\acute{y}T = \frac{100}{1+\exp(\hat{\lambda}(T-\hat{T}_0))} + (yT - \hat{y}T)\forall\ T \qquad \text{Eqn. 3}$$

While the data value of 100 is used here, there may be more appropriate values for some datasets, or an initial scaling of the raw data to maximum value 100 might be appropriate. The issue is that the residuals could be somewhat overwhelmed if an inappropriate value were used; however, the feature extraction discussed below should prevent any major problems in practice.

Principal Component Extraction 2

The normalized data is now on a comparable basis for each data set, but there is normally far too much information in the full melt curve to usefully proceed. As stated earlier some or all of the five parameters of Eqn 2 can be used as features; however, this may fail to capture some important properties of the data (e.g., heterozygosity).

In a preferred embodiment, a more empirical approach is taken. Firstly, the differences of the data are utilized. This is because the differences between melt curves are accentuated on the rate of change scale. Secondly, a form of principal components analysis is used to extract a small number of features for each (differenced) melt curve. Principal components analysis selects the linear combination of the data vector that shows the most variation amongst the samples as the first principal component.

Again, mathematically let $z_i = \acute{y}_{Ti} - \acute{y}_{Ti-1}$ where $T_{i-1}$ is the temperature measured immediately before temperature $T_i$. Then the first principal component score for this sample is:

$$PC_1 = \sum_i a_i z_i \qquad \text{Eqn. 4}$$

where the $\{a_i\}$ are chosen so that $PC_1$ shows maximum variation across all samples. Subsequent principal components can then be defined as those linear combinations that maximise variability subject to being orthogonal to preceeding components. For example:

$$PC_2 = \sum_i b_i z_i \qquad \text{Eqn. 5}$$

where the $\{b_i\}$ are chosen so that $PC_2$ shows maximum variation across all samples and $\Sigma_i\ a_i b_i = 0$. The calculations for principal components essentially involve an eigenvalue problem, and these can be computed efficiently using singular value decomposition. (See for example Golub [G. H. Golub and C. F. Van Loan, "Matrix Computations", Johns Hopkins University Press, 1996 (3rd Edition)], or Press et. al. [W.H. Press, B. P. Flannery, S. A. Teukolsky and W. T. Vetterling, "Numerical Recipes in C", Cambridge University Press, 1988]; both incorporated herein by specific reference.) Since there is a principal component loading for each temperature (e.g., the $a_i$ corresponds to the i-th temperature $T_i$), it is possible to think of the $\{a_i\}$ as a function of temperature, and plot them.

In the alternative, it is also possible to specify further that these principal component functions (or curves) be somewhat smooth. This leads to an analysis known as smooth principal components (see Ramsay and Silverman [J. O. Ramsay and B. W. Silverman, "Functional Data Analysis", Springer, 1997], incorporated herein by specific reference). This leads to a modified form of singular valued decomposition.

Once the principal component scores are calculated, a number are chosen to be used. In the present examples, two or three has proven most useful.

Cluster Analysis and the Gap Statistic 4

The aim of Cluster Analysis is to find de-novo groups in the data without any samples having known labels. Two main types of cluster analysis can be used:

- k-means cluster analysis has the advantage of relatively simple implementation, although the disadvantage of requiring the number of clusters desired to be prespecified, and initial cluster centres defined.
- single link hierarchical clustering. Hierarchical clustering produces a complete set of nested clusters, starting with each sample in its own cluster up to a single cluster containing all samples. There are multiple variants with different degrees of efficient implementation difficulty (although for a maximum of 96 samples a brute force approach is likely sufficient). The number of clusters desired is chosen post-hoc.

k-means:

The k-means clustering algorithm proceeds as follows. Suppose one requires k clusters and has proposed k cluster centres—One possibility are randomly chosen samples from the dataset. Each sample is then allocated to the nearest cluster centre. The centres are then recalculated as the centres of the clusters defined by the allocated samples, and the algorithm iterates. There are a number of further modifications that can be made to this basic algorithm.

Hierarchical Clustering

As mentioned above, hierarchical clustering starts out by defining n clusters (where there are n samples), with each sample in its own cluster. Clusters are then merged until only one cluster remains containing all the samples. The hierarchy of merging clusters can then be used to find a set of clusters for any number k of desired clusters. Generally, at each stage the closest two clusters are merged. To do this one needs to define the distance between clusters, given that there is a distance between samples. Three of the common definitions are:

- single or minimum link where the distance between two clusters is the minimum of the distances between the pairs of samples with a sample in each cluster.
- complete or maximum link where the distance between two clusters is the maximum of the distances between the pairs of samples with a sample in each cluster.
- average link where the distance between two clusters is the average of the distances between all pairs of samples with a sample in each cluster.

The Gap Statistic

The choice of the number of clusters can be a difficult aspect of cluster analysis. The gap statistic was proposed [R. Tibshirani, G Walther and T. Hastie, "Estimating The Number Of Clusters In A Data Set Via The Gap Statistic", J. R. Statist. Soc. B, 63(2), pp. 411-423, 2001], incorporated herein by specific reference, as a possible guide to choosing the number of clusters. The main idea is to look at a measure of cluster quality and compare it to that for similar data known to not have any real clusters. The measure of cluster quality used is generally the within cluster sum of squares;

$$W_k = \sum_{j=1}^{k} \sum_{i \in c_j} \|x_i - \overline{x}_j\|^2 \qquad \text{Eqn. 6}$$

where $C_j$ is the j-th cluster, and $\overline{x}_j$ is its centre (mean). One choice of reference data is data uniformly randomly generated over a box containing the original data. This is often done in a principal component space, but that is not necessary for this application, as our features are already smoothed principal component scores. The algorithm is therefore is then:

Step 1: cluster the observed data, varying the number of clusters k=1, 2, ..., K for some maximum K, and compute $W_k$ for each k.

Step 2: generate B random reference data sets and cluster each as in Step 1, computing $W_{kb}$ for k=1, 2, ..., K and b=1, 2, ..., B.

Step 3: compute the Gap statistic and standard error for each k:

$$\text{Gap}(k) = (1/B) \sum \log(W_{kb}) - \log(W_k) \qquad \text{Eqn. 7}$$

$$s_k = \sqrt{(1 + 1/B)\sqrt{\{(1/B)\sum_b (\log(W_{kb}) - (1/B)\sum_b \log(W_{kb}))^2\}}}; \qquad \text{Eqn. 8}$$

Step 4: choose the number of clusters k' to be the smallest k such that $\text{Gap}(k) \geq \text{Gap}(k+1) - s_{k+1}$ There are two outstanding issues with the clustering of samples. The first is the choice of number of principal component dimensions to use, and the second is the automated use of the gap statistic. Initial tests show suitable results can be achieved using a gap statistics on two and three dimensions. Generally it appears that when there are a larger number of small clusters three dimensions will be required, but that for a smaller number of larger clusters, it is better to carry out the cluster analysis in two dimensions. The automated choice of the number of clusters using the gap statistics has proved problematic when clusters are small, and therefore it is recommended that user intervention be allowable, and that the resultant gap statistic curves be used as a guide.

Bayes Information Criterion (BIC)

k-means cluster analysis can be seen as an (approximate) maximum likelihood estimator, when the clusters are regarded a spherically normally distributed with the same (diagonal) variance matrix. This is useful, because in a maximum likelihood setting when comparing models with an increasing number of parameters p, model selection is sometimes done using Bayes Information Criterion (BIC). Generally, the formula used for BIC is $$\log \text{lik}_{max} - p \log(n)/2 \qquad \text{Eqn. 9}$$

where $\log \text{lik}_{max}$ is the maximized log likelihood for a given number of parameters p and n is the number of samples. This criterion (BIC) is then generally maximized over p to choose the model.

In our case this becomes, $$-n(d \log(2\pi)/2 + d \log(\hat{a}^2)/2) - dn/2 - n \log(k) - (kd+1)\log(n)/2 \qquad \text{Eqn. 10}$$

where d is the dimensionally of the data, k is the number of clusters and á is the estimated variance common to all dimensions and clusters.

The reason for considering BIC is its ease of generalization to the supervised case; however, this has not proven useful in practice.

Classification with Some Known Samples

The issue of classifying unknown samples into known groups where samples from the known groups are included in the same run is more well understood than de novo generation of groups. One suitable method for classification with known samples is Linear Discriminant Analysis.

Linear Discriminant Analysis

Linear discriminant analysis arises as the preferred classifier when the data has a multivariate normal distribution, and each class has the same variance/covariance matrix but differing means. In practice, even when these assumptions may not hold, linear discriminant analysis (LDA) is an effective and efficient classifier.

Let x be the p principal component scores of a single sample (i.e., either p=2 or p=3) from a set. Then LDA assumes that the density function of x is given by:

$$f_k(x) = \frac{1}{(2\pi)^{p/2} |\Sigma|^{1/2}} \exp\left\{-\frac{1}{2}(x-\mu_k)^T \Sigma^{-1} (x-\mu_k)\right\} \qquad \text{Eqn. 11}$$

where $\mu_k$ is the mean (centre) of class k and $\Sigma$ is the variance/covariance matrix of all the classes. Both $\mu_k$ and $\Sigma$ need to be estimated. When the number of known examples in each group is two or more then formally these parameters can be estimated using the known examples. However, it would be desirable to have more known samples than this—perhaps five or more per group would produce better results. When there are no known samples per group, then cluster analysis can be utilized (unsupervised). When there is only one known sample per group (or, in practice, for other small number of known samples), two possible approaches can be used:

Use a predefined $\Sigma$: This could be fixed, for example an identity matrix when LDA collapses to nearest neighbour classification, or it could be determined from a previous experiment where more known samples were run. In the latter case, run-to-run variation would need to be considered.

Use a staged approach. Allocate the samples to the appropriate groups using the approach above, and then estimate $\Sigma$ assuming the allocations are correct. This is likely to be optimistic in the sense that the estimated variances will be a little too small. However, firstly, when the groups are well separated in principal component space, the degree of optimism will be small. Secondly, the optimism may not have much impact on the posterior probabilities which are used to determine the final group allocation of unknown samples. It is possible to use a blending of a fixed $\Sigma$ and one estimated from the known samples. This is known as regularized discriminant analysis.

Posterior Class Probabilities

The posterior class probabilities are the probabilities that each sample is a member of each group assuming that the sample is a member of one of the groups (i.e., these are the conditional probabilities given that the sample is in one of the groups). It can be shown that these are estimated by:

$$p_k(x) = \frac{f_k(x)}{\sum_j f_j(x)} \qquad \text{Eqn. 12}$$

Where $f_k(x)$ is defined above and the sum is taken over all groups. An unknown sample would be allocated to the group with the largest posterior class probability $p_k(x)$.

Typicalities

The posterior class probabilities tell which group a sample is most likely a member of, given that it is a member of at least one of them. A typicality index tells how consistent an unknown sample is with any of the groups. A common measure of typicality stems from the observation that:

$$F_k(x) = \frac{(n_k)(n-K-p+1)}{(n_k+1)p(n-K)}(x-\mu_k)^T \sum{}^{-1} (x-\mu_k)$$ Eqn. 13 has an F-distribution on p and n−g−p+1 degrees of freedom. Thus setting:

$$a_k(x) = \text{Prob}(F >= F_k(x))$$ Eqn. 14

$$a(x) = \max_k a_k(x)$$ Eqn. 15 it is possible to interpret a(x) as a probability that x is from any of the groups.

The above observation using an F-statistic is complex but not statistically most valid. An alternative, approximate, method is to note that, $$(x-\mu_k)^T \Sigma^{-1} (X-\mu_k)$$ Eqn. 16 would have a $\chi^2$ distribution if $\mu$ and $\Sigma$ were assumed known. This is a more appropriate form to utilize.

Choice of Dimension in the Supervised Case

The choice of dimension in the supervised case requires some guidance. Intuitively one would want to use the number of dimensions that produces lowest number of misclassifications. The number of misclassifications can be estimated using cross-validation. Cross-validation involves leaving a (known) sample, and using the remainder to build a classifier. The left out observation is then classified and any errors counted. This process is repeated for the dimensions of interest and the dimensionality with the lowest error rate chosen.

The error rate tends to be quite discrete, so often the same number of errors are made in two or more dimensionalities. A less discrete approach is to look at the posterior possibilities of the true classes for the known cases. By multiplying these probabilities (or summing the logs) over all the known cases, an overall measure of the quality of the classification can be obtained. In principle, also a cross-validation approach can be used to do this.

It is reported that both of these measures essentially return to zero (the best result) for all dimensions, thus not aiding the choice of dimensions. This is probably due to the relatively well separated clusters.

In the following, a second preferred embodiment of the invention is described by means of a concrete Example. Thereby, five different HRM data sets are used. Four of the data sets are generated on a Rotor-Gene 6000 using 25 μL volumes containing master mix and template. These included; thirty two known replicates of each allele for the human factor V Leiden (G1619A) polymorphism, which are run using 1× AmpliTaq Gold SYBR Green master mix (Applied Biosystems, USA), 300 nM each primer and 25 ng of template DNA. Five replicates of each allele of a synthetic A to T SNP template are run using 1× HRM Sensi Mix (Bioline), 1× EvaGreen fluorescent intercalating dye (Biotium, USA), 300 nM each primer and 20 ng of template. Three replicates of each of five alleles for the human BRCA1 exon 11-6 fragment are run using Titanium taq polymerase with 1× SYTO-9 fluorescent green intercalating dye (Invitrogen, USA) (data courtesy Centre for Human Genetics, Leuven, Belgium). Finally, a complex DNA fingerprinting assay for the human TH01 short tandem repeat (STR) sequences is analysed. Eight known alleles are run with replicates ranging from 5-8 samples (data courtesy Dr. David French, LGC, Teddington, UK).

Normalization

Raw HRM curves are normalized using two distinctly different methods. The first method applies a scaling of the curve to a line of best fit such that the highest fluorescence value is equal to 100 and the lowest equal to zero. Two regions of the melt data, prior and following melt curve transition, are selected and the average fluorescence and slope of the curve calculated and applied in the normalization. Further iterations of this method could also include normalizing for exponential slope in the defined regions (see WO 2007/035806 A2).

The second method applies the Levenberg-Marquardt least-squares estimation of non-linear parameters using a defined ideal model of a double-stranded melt curve as described above with respect to the first preferred embodiment of the invention. As mentioned above, an ideal melt curve can be represented by Eqn. 1.

However, HRM curves consist of more complex components including background noise and fluorescence changes due to temperature. As described above, these parameters are taken into consideration in Eqn. 2 which is used as model curve and the Levenberg-Marquardt algorithm is applied to run an iterative process of fitting the five parameters to the model such that the sum of squares of the deviations becomes minimal for each individual raw curve. Residuals from the model are computed and added back to the idealized melt curve to produce the normalized data.

Mathematically, suppose {yT} is the sequence of fluorescence values from the raw melt curve. Let {ŷT} be the values from Eqn. 2 after fitting to the raw data. The normalized data {ỹT} is defined by Eqn. 3.

Note that the value 100 is used here but there may be more appropriate values for some datasets, or perhaps an initial scaling of the raw data to maximum value 100 might be appropriate. The issue is that the residual could be somewhat swamped if an inappropriate value is used, however, the feature extraction discussed in the next section seems to prevent any major problems.

Both methods of normalization described are compared using two HRM data sets containing various types of alleles of differing fragment length and complexity of sequence. The objective of the exercise is to determine which method provides the best representation of the known genotypes in the analysed data using unsupervised cluster analysis.

Principal Component Analysis

To accentuate the differences between genotypes, the normalized melt curves are differentiated so as to observe the scale of rate of change. To further tease more information out of the curves, a subtraction plot is generated using a median composite curve of all the analysed curves as the control. This method of subtraction plotting removes the need for a known set of controls and thus enables the user to detect unknown genotypes that reside within the data set. From the subtraction plot a form of principle component analysis is used to extract a small number of features for each curve. Principal component analysis selects the linear combination of the data vector that shows the most variation amongst the samples as the first principal component (PC) (see [Jolliffe I. Principal component analysis, Springer, $2^{nd}$ Edition]; incorporated herein by specific reference). Subsequent PCs account for as much of the remaining variability as possible. Each individual sample has a certain amount of loading to each of the PCs, which is plotted to generate a cluster. Most data sets only require the first three PCs as most of the remaining variance in the other PCs will be attributed to noise. The selection of the appropriate number of PCs to use is described below.

Cluster Analysis of Unsupervised Data

The aim of unsupervised cluster analysis is to find de-novo groups in the data without any samples having known labels. Single link hierarchical clustering can only be used when the number of clusters (k) is defined but does not allow for the detection of the preferred number of clusters. To allow for this, the method of k-means cluster analysis is selected. K-means provides clusters by centring on a mass of sample members (see [Hartigan J A. and Wong M A., Algorithm AS 136: A k-means clustering algorithm, Appl. Statist., 1979; 28(1): 1000-108]; incorporated herein by specific reference). Alone, it is unable to provide the preferred number of clusters, rather it defines clusters based on a cluster number. To determine preferred choice of clusters k-means are combined with the Gap statistic (see [Tibshirani R, Walther G, and Hastie T., Estimating the number of clusters in a data set via the gap statistic, J. R. Statist. Soc., 2001; 63: 411-423]; incorporated herein by specific reference). The idea is to look at a measure of cluster quality and compare it to that of similar data known to not have any real clusters. The measure of cluster quality used is the within cluster sum of squares as defined in Eqn. 6 above.

Where $C_j$ is the j-th cluster, and $\bar{x}_j$ is its centre (mean). The algorithm, firstly, clusters the data, varying the number of clusters (k=1, 2, . . . , K) to compute $W_k$. Secondly, it generates B random reference data sets and clusters each as in Step 1, computing $W_{kb}$ for k=1, 2, . . . , K and b=1, 2, . . . , B. Thirdly, it computes the Gap statistic and standard error for each k applying the formulae Eqn. 7 and Eqn. 8 (see above).

Finally, it selects the number of clusters $\hat{k}$ to be the smallest k such that the Gap(k)$\geq$Gap(k+1)$-s_{k+1}$. Graphically, the preferred cluster number is typically observed as the point of maximum change in Gap value that is preceded with a plateau with subsequent cluster numbers vs. Gap values. One outstanding issue with using the Gap is the selection of PC dimensionality; therefore, the Gap statistic is plotted for both two and three PC. The preferred selection of PC number is the Gap plot with the highest transitional variation.

With respect another exemplary embodiment of the invention, FIG. 1 shows the steps in the process for HRM analysis in a flow chart. The process begins with normalization 1, which is followed by extracting the principal components (PCs) 2. If the number of alleles is unknown 3 unsupervised cluster analysis 4 that combines k-means and the gap statistic is utilized. If only one control per allele is known then a nearest neighbour classifier is applied 5 and the grouped samples recomputed using linear discriminant analysis (LDA). When two or more controls per allele are provided then LDA 6 is applied in a supervised analysis.

Another alternative to the Gap statistic is the use of the Bayes Information Criterion, which is a parametric method statistic useful for model selection (see [Schwarz, G. 1978. Estimating the dimension of a model, Annals of Statistics, 1978; 6(2):461-464]; incorporated herein by specific reference). The general formula used is Eqn. 9 (see above) where log lik$_{max}$ is the maximum log likelihood for a given number of parameters p and n is the number of samples. The BIC is then generally maximised over p to choose the model, which in our case is the number of clusters. Both methods of cluster and PC selection are compared using selected HRM data sets.

Discriminant Analysis of Supervised Data

Classification of unknown samples into known groups using known samples as controls is achieved using linear discriminant analysis (LDA). LDA arises as a preferred classifier when the data have a multivariate normal distribution, and each class has the same variance/covariance matrix but differing means (see [Ye J, Li T, Xiong T, Janardan R., Using uncorrelated discriminant analysis for tissue classification with gene expression data, IEEE/ACM Trans. Comput. Biol. Bioinform, 2004; 1(4):181-90]; incorporated herein by specific reference). In practice, even when these assumptions do not hold true, LDA is an effective and efficient classifier. Let x be the p PC scores of a single sample (either p=2 or p=3) from a set. Then, LDA assumes that the density function of x is given by Eqn. 11.

Where, $\mu_k$ is the mean (centre) of class k and $\Sigma$ is the variance/covariance matrix of all the classes. Both $\mu_k$ and $\Sigma$ need to be estimated. When the number of known examples in each group is 2 or more then formally these parameters can be estimated using known examples (training set). However, it would be desirable to have more known samples than this (more than five controls per group). When there is only one sample per group it is deferred to a nearest neighbour classification, then assuming the allocations are correct estimate $\Sigma$ and recompute the LDA.

The choice of PC dimensionality using a supervised data set is achieved using a cross-validation to find the number of PCs that produces the lowest number of misclassifications. Cross-validation involves leaving a known sample, and using the remainder to build a classifier. The left out observation is then classified and any error counted. This process is repeated for each PC number and the dimensionality with the lowest error rate is chosen. Often the same numbers of errors are made in two or three PC; therefore, a less discrete approach of looking at the posterior probabilities of the true classes for the known cases can be used. By multiplying these probabilities over all the known cases an overall measure of the quality of the classification is obtained. In an embodiment of the inventive software, the PC with the lowest "Error" value should be chosen. However, if both errors are the same then the PC with the lowest "Posterior" calculation value is the preferred to use. If both values are equal to zero then the lower PC should be selected.

Posterior Class Probabilities and Typicalities

Posterior class probabilities are the probabilities that each sample is a member of each group assuming that the sample is a member of one of the groups. It can be shown that these are estimated by Eqn. 12 (see above) where $f_k(x)$ is defined above in Eqn. 11 and the sum is taken over all groups. An unknown sample would be allocated to the group with the largest posterior class probability $p_k(X)$.

Posterior class probabilities tell which group a sample is most likely a member of, given that it is a member of at least one of them. A typicality index tells how consistent an unknown sample is with any of the groups. A common measure of typicality stems from the observation that the result of Eqn. 13 has an F-distribution on p and n−K−p+1 degrees of freedom. Thus setting Eqn. 14 and Eqn. 15, it is possible to interpret a(x) as a probability that x is from any of the groups.

Software

The work flow diagram of an embodiment of the inventive software is shown in FIG. 1. Raw HRM plots from the Rotor-Gene software are imported into the software using comma-delineated spread sheets, with syntactic analysis (parsing) to ensure the correct data is analysed. A cropping function is made available to allow the user to avoid regions of non-specific amplification products. To ensure effective normalization as much of the pre and post melt data is made available for analysis. All no template controls (NTC) are automatically removed from the analysis as the lack of melt curve features affects the normalization. Following sample selection, the user can select between analysing supervised or unsupervised data sets. Selecting "unsupervised" enabled the k-means clustering and Gap statistic algorithms, with the software selecting the most appropriate cluster number and PC number to use. Using the "supervised" feature allowed the user to select the appropriate controls for each genotype. If more than two controls were used for each group, LDA would be used and the appropriate number of PC determined via the cross-validation function. Having only one control would activate the nearest neighbour classification of samples into groups, which is proceeded by a re-computation using LDA.

The clusters are graphically plotted using the loading scores of each PC for all samples (e.g., PC1 vs. PC2) for both supervised and unsupervised methods. An ellipsoid representing the cluster variance/covariance following classification is also drawn. Unknown samples are classified into each cluster group with posterior probabilities and typicalities being calculated for all samples.

Results

With regard to the evaluation of normalization methods, the first evaluation of the software is the appropriate choice of normalization technique. Using two sets of HRM data it is set out to determine how well each method could normalise the melt curves without losing too much information that would be required for further interpretation using PC extraction and clustering. The observed clustering, posterior probabilities and typicalities for unsupervised analysis are compared for the predefined genotypes and replicates, which are referred to pseudo-unknowns. Using the normalization process of fluorescence scaling to a line of best fit it is observed that the data retained most of the curve features post normalization (see FIG. 2A). Such retention in curve features is not so evident using the Levenberg-Marquardt algorithm, which results in the characteristic heteroduplex curve double inflexion to disappear (see FIG. 2B). Despite such observations using the Levenberg-Marquardt algorithm, the clustering and calling of unknown samples and clusters is still effective for well defined melt curve separations, such as for the factor V leiden (G1691A) data set. However, as can be derived from Table 1 below, for one of the data sets containing low resolution melt curve polymorphic variants (BRCA1 exon 11-6), loss of curve feature following normalization using the Levenberg-Marquard algorithm results in incorrect clustering and calling of pseudo-unknowns using unsupervised analysis. Using the fluorescence scaling to line of best fit model, all clusters and samples are called correctly with high posterior probabilities and typicalities.

TABLE 1

Unsupervised Analysis using Scaling Fluorescence and Levenberg-Marquardt Algorithm Normalization

| Sample | Scaling Fluorescence | | | Levenberg-Marquardt Algorithm | | |
|---|---|---|---|---|---|---|
| | Cluster Number[#] | Probability | Typicality | Cluster Number[#] | Probability | Typicality |
| 1.1 | 4 | 1.00 | 0.47 | 3 | 1.00 | 0.59 |
| 1.2 | 4 | 1.00 | 0.26 | 3 | 1.00 | 0.18 |
| 1.3 | 4 | 1.00 | 0.99 | 3 | 1.00 | 0.44 |
| 2.1 | 1 | 1.00 | 0.98 | 3 | 1.00 | 0.07 |
| 2.2 | 1 | 1.00 | 0.98 | 3 | 1.00 | 0.24 |
| 2.3 | 1 | 1.00 | 0.68 | 3 | 1.00 | 0.99 |
| 3.1 | 3 | 1.00 | 0.60 | 4 | 1.00 | 0.16 |
| 3.2 | 3 | 1.00 | 0.40 | 4 | 1.00 | 0.60 |
| 3.3 | 3 | 1.00 | 0.41 | 4 | 1.00 | 0.54 |
| 4.1 | 2 | 1.00 | 0.80 | 1 | 1.00 | 0.99 |
| 4.2 | 2 | 1.00 | 0.88 | 1 | 1.00 | 0.93 |
| 4.3 | 2 | 1.00 | 0.74 | 1 | 1.00 | 0.97 |
| 5.1 | 5 | 1.00 | 0.85 | 2 | 1.00 | 0.92 |
| 5.2 | 5 | 1.00 | 0.42 | 2 | 1.00 | 0.73 |
| 5.3 | 5 | 1.00 | 0.66 | 2 | 1.00 | 0.95 |

[#]Cluster number is randomly determined using the unsupervised analysis feature. For the purpose of this result there should be five clusters determined and the replicates for each allele should have the same cluster number.

Figure 2:
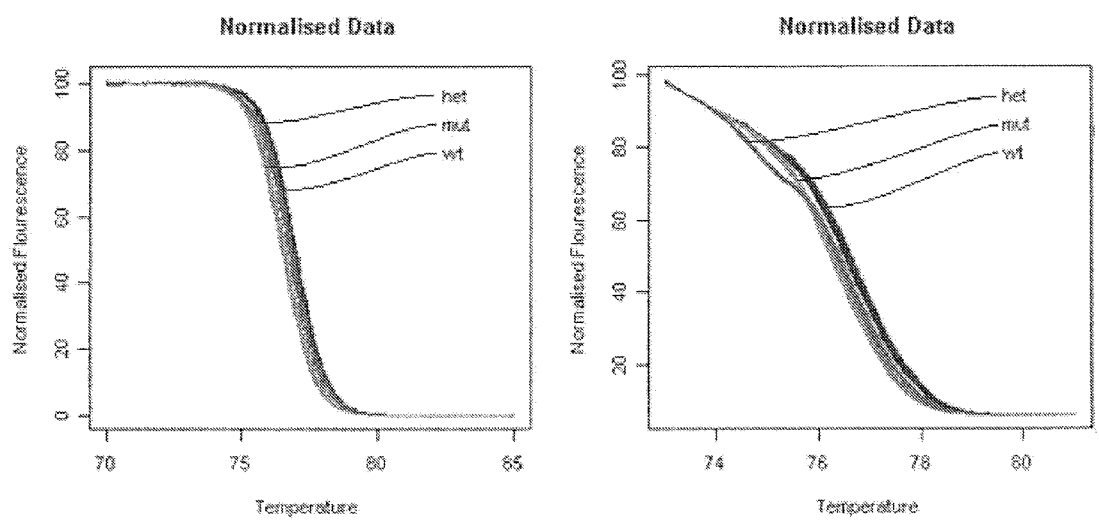
FIG. 2 shows normalization curves for Factor V Leiden (G1691A) genotype.

In FIG. 2, normalization curves for Factor V Leiden (G1691A) genotype are shown. Using the scaling of fluorescence to a line of best fit normalization method allows all three genotypes to be clearly discriminated with retention of the double inflection, which represents the heteroduplexes (FIG. 2, left graph). Conversely, normalization using the Levenberg-Marquardt least squares estimation of non-linear parameters results in the loss of the heteroduplex double inflection (FIG. 2, right graph). Although there is a loss of curve feature in the latter method, no impact on supervised or unsupervised analysis is observed for this HRM data set. Therefore, scaling fluorescence to a line of best fit is selected as the preferred normalization method.

Figure 3A:
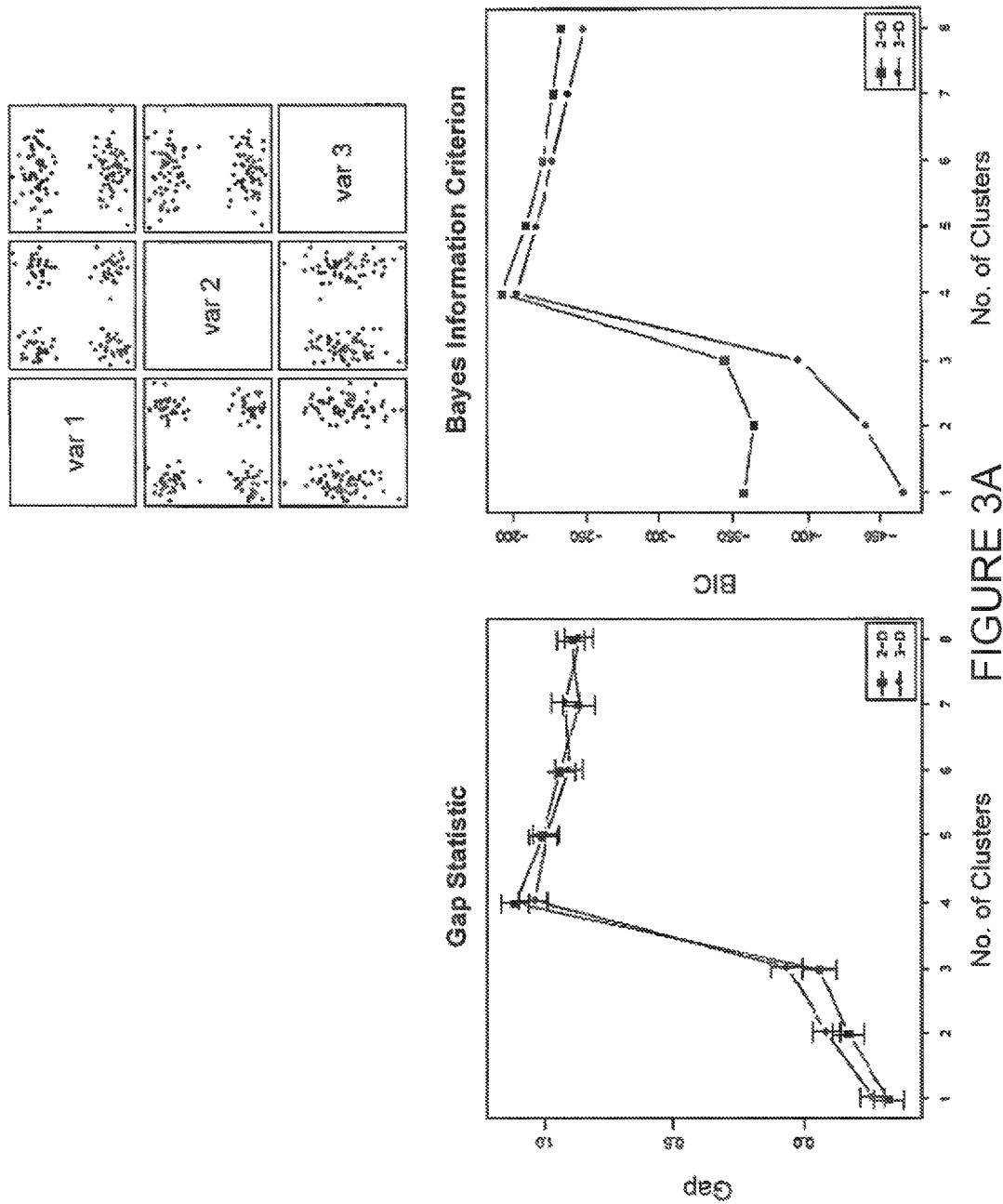
FIGS. 3A and 3B show determining preferred principal component (PC) dimensionality for unsupervised analysis.
Figure 3B:
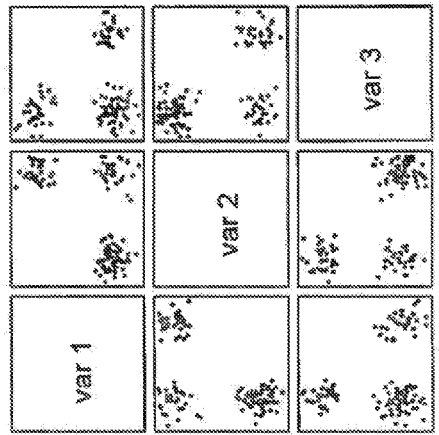
Figure 3B:
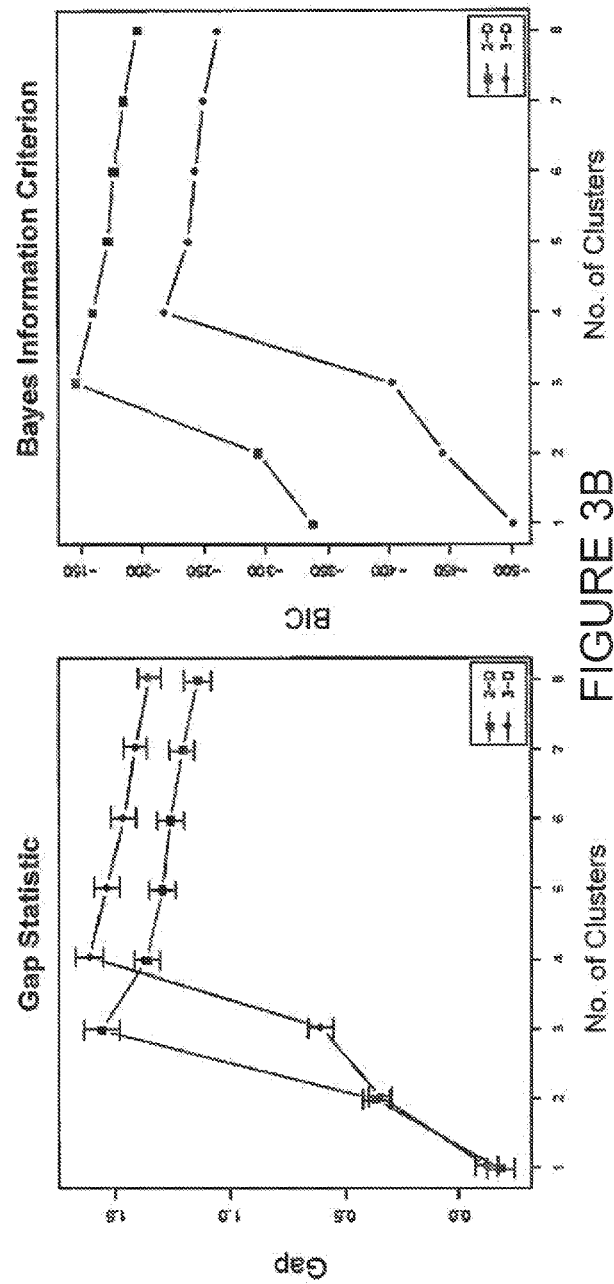

With regard to the evaluation of the preferred cluster determination, two alternative methods for determining the preferred numbers of clusters for k-means were evaluated: the Gap statistic and BIC. A pair of simulated data sets containing four clusters is used such that the first data set has the four cluster centres aligned in the third PC so that no information is contributed by that dimension. FIGS. 3A and 3B show that plot of simulated data, the Gap statistic and BIC plots. Both methods slightly favour the two PC dimension solution for four clusters. The second data set has one of the clusters moved into the third PC dimension and behind another cluster so that the dimension adds required information. The Gap statistic slightly favours the choice of four clusters in the third dimension while the BIC strongly, but incorrectly, favours three clusters in two dimensions (see FIG. 3B).

Turning again to FIGS. 3A and 3B regarding the software, the determining of optimum PC dimensionality for unsupervised analysis is shown. Using a simulated dataset of four clusters the first set aligns the clusters in the third dimension so that no information is contributed by that dimension (see FIG. 3A). Using the gap statistic and Bayes information criterion (BIC) for optimum cluster determination, demonstrates that both methods favour four clusters in two dimensions. When the four clusters are aligned such that the third dimension provided information, only using the gap statistic are four clusters in the third PC dimension favoured (see FIG. 3A). Using the BIC results in three clusters being favoured in two dimensions. The result clearly demonstrates that the gap statistic is the preferred method to use in the software.

Figure 4:
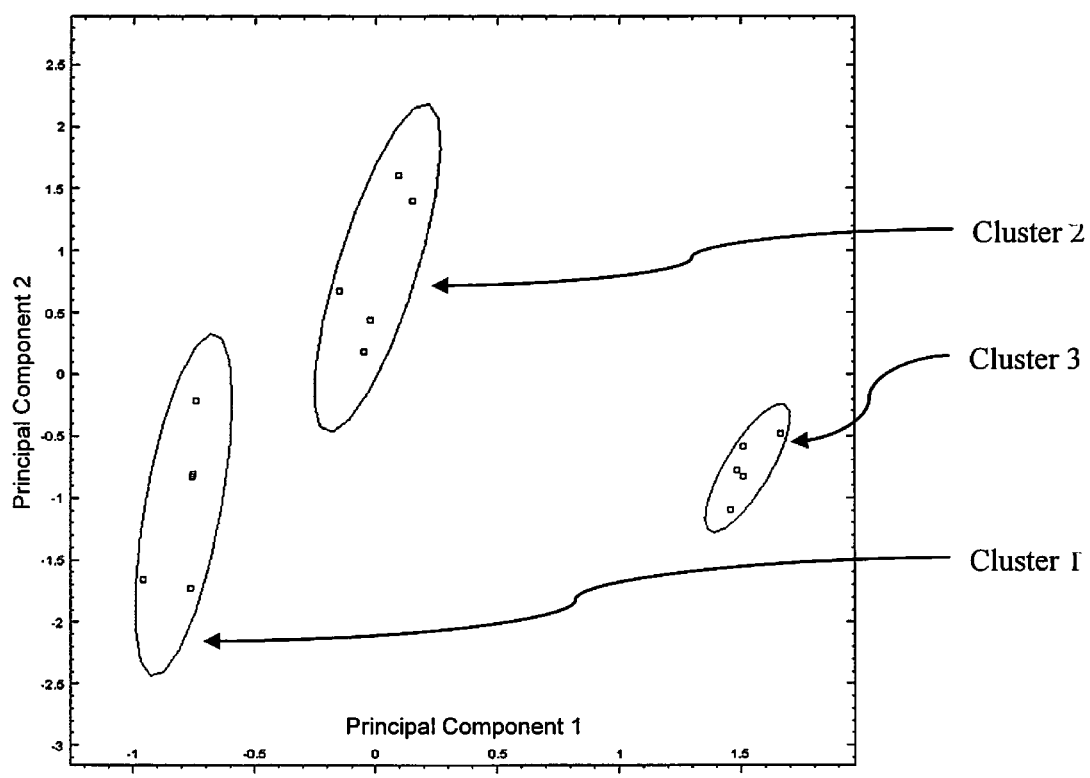
FIG. 4 shows synthetic A to T SNP unsupervised clustering.

With regard to the experimental data, having determined the appropriate methods for achieving preferred results, the software is evaluated using a synthetic A to T substitution assay data set and the human TH01 STR assay developed by David French of LGC (Teddington, UK). The software is capable of clustering all three genotypes of the synthetic A to T polymorphism data set calling all pseudo-unknowns correctly into their respective genotypes when using the unsupervised analysis feature (see FIG. 4). Although the Gap statistic is not as defined as previous data sets, it correctly favours three clusters in two PC dimensions. As can be derived from Table 2 below, when the supervised analysis feature is applied and the first two samples of each genotype selected as controls, the software again is capable of correctly calling all the pseudo-unknowns.

TABLE 2

Supervised Analysis Results for A to T SNP Assay

| Sample | Probability A | Probability T | Probability AT | Typicality |
|---|---|---|---|---|
| A.1* | 1.00 | 0.00 | 0.00 | 0.46 |
| A.2* | 1.00 | 0.00 | 0.00 | 0.84 |
| A.3* | 1.00 | 0.00 | 0.00 | 0.79 |
| A.4 | 1.00 | 0.00 | 0.00 | 0.62 |
| A.5 | 0.99 | 0.00 | 0.01 | 0.17 |
| T.1* | 0.00 | 1.00 | 0.00 | 0.42 |
| T.2* | 0.00 | 1.00 | 0.00 | 0.70 |
| T.3* | 0.00 | 1.00 | 0.00 | 0.45 |
| T.4 | 0.17 | 0.83 | 0.00 | 0.07 |
| T.5 | 0.10 | 0.90 | 0.00 | 0.10 |
| AT.1* | 0.00 | 0.00 | 1.00 | 0.23 |
| AT.2* | 0.00 | 0.00 | 1.00 | 0.43 |

TABLE 2-continued

Supervised Analysis Results for A to T SNP Assay

| Sample | Probability A | Probability T | Probability AT | Typicality |
|---|---|---|---|---|
| AT.3* | 0.00 | 0.00 | 1.00 | 0.89 |
| AT.4 | 0.00 | 0.00 | 1.00 | 0.21 |
| AT.5 | 0.00 | 0.00 | 1.00 | 0.41 |

*Samples are selected as controls.

Referring again to FIG. 4, synthetic A to T SNP unsupervised clustering is shown. All pseudo-unknowns for the A (Cluster 1), T (Cluster 2) and AT (Cluster 3) are correctly clustered and called into the respective genotypes using the unsupervised analysis feature. Clusters are highlighted by ellipsoids that represent the variance/covariance of the classified samples in a two PC dimension plot. A to T polymorphisms are the most difficult to discriminate using HRM as the difference between homozygote alleles can be less than 0.1° C.

Figure 5:
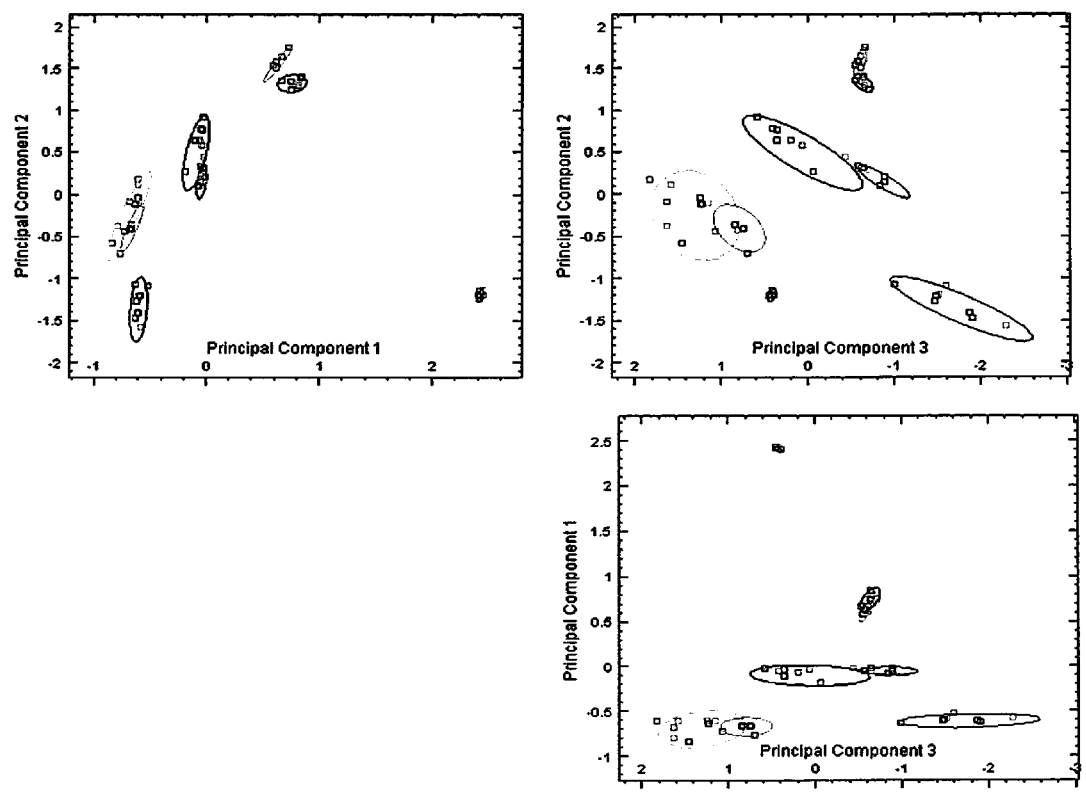
FIG. 5 shows TH01 STR unsupervised clustering.

Unsupervised analysis of the TH01 STR data set yields eight clusters that are observed in three PC dimensions (see FIG. 5). All pseudo-unknowns are called correctly into each of their respective allele repeats with high posterior probabilities and typicalities. Similarly, using supervised analysis, selecting the first three samples as controls, provides correct calling of all but one of the pseudo-unknowns. The sample that is called incorrectly has a posterior probability value of 50%. The software compares supervises result for the TH01 STR data set to a result obtained using the HRM analysis of the Rotor-Gene Q version 1.7 software. As can be derived from Table 2 below, the first sample of each genotype is selected as the control and the percentage confidence limit is set to 70%. A number of the samples can not be correctly called using the Rotor-Gene Q HRM analysis software when a 70% confidence percentage is applied.

TABLE 3

Supervised Analysis Results for TH01 STR HRM Data Set

| Sample | Cluster | Typicality | 7/10 | 9/9.3 | 9.3/9.3 | 9.3/10 | 7/9.3 | 6/9.3 | 7/9 | 7/8 |
|---|---|---|---|---|---|---|---|---|---|---|
| LR1* | 7/10 | 0.56 | 1.00 | | | | | | | |
| LR2* | 7/10 | 0.11 | 1.00 | | | | | | | |
| LR3* | 7/10 | 0.78 | 1.00 | | | | | | | |
| LR4 | 7/10 | 0.06 | 1.00 | | | | | | | |
| LR5 | 7/10 | <0.01 | 1.00 | | | | | | | |
| LR6 | 7/10 | 0.04 | 1.00 | | | | | | | |
| LR7 | 7/10 | <0.01 | 1.00 | | | | | | | |
| LR8 | 7/10 | 0.15 | 1.00 | | | | | | | |
| CC1* | 9/9.3 | 0.04 | | 0.99 | | | | | 0.01 | |
| CC2* | 9/9.3 | 0.76 | | 1.00 | | | | | | |
| CC3* | 9/9.3 | 0.17 | | 1.00 | | | | | | |
| CC4 | 9/9.3 | 0.11 | | 1.00 | | | | | | |
| CC5 | 9/9.3 | 0.24 | | 1.00 | | | | | | |
| CC6 | 9/9.3 | 0.99 | | 1.00 | | | | | | |
| CC7 | 9/9.3 | 0.87 | | 1.00 | | | | | | |
| JNH1* | 9.3/9.3 | 0.24 | | | 1.00 | | | | | |
| JNH2* | 9.3/9.3 | 0.53 | | | 1.00 | | | | | |
| JNH3* | 9.3/9.3 | 0.83 | | | 1.00 | | | | | |
| JNH4 | 9.3/9.3 | 0.05 | | | 1.00 | | | | | |
| JNH5 | 9.3/9.3 | 0.01 | | | 1.00 | | | | | |
| JNH6 | 9.3/9.3 | 0.02 | | | 1.00 | | | | | |
| JNH7 | 9.3/9.3 | <0.01 | | | 1.00 | | | | | |
| AG1* | 9.3/10 | 0.99 | | | | 1.00 | | | | |
| AG2* | 9.3/10 | 0.96 | | | | 1.00 | | | | |
| AG3* | 9.3/10 | 0.96 | | | | 1.00 | | | | |
| AG4 | 9.3/10 | 0.27 | | | | 1.00 | | | | |
| AG5 | 9.3/10 | <0.01 | | | 0.13 | 0.87 | | | | |
| AG6 | 9.3/10 | 0.04 | | | 0.01 | 0.99 | | | | |
| AG7 | 9.3/10 | 0.03 | | | 0.01 | 0.99 | | | | |
| AG8 | 9.3/10 | 0.16 | | | | 1.00 | | | | |
| CR1-1* | 7/9.3 | 0.99 | | | | | 0.99 | 0.01 | | |
| CR1-2* | 7/9.3 | 0.96 | | | | | 0.99 | 0.01 | | |

TABLE 3-continued

Supervised Analysis Results for TH01 STR HRM Data Set

| Sample | Cluster | Typicality | 7/10 | 9/9.3 | 9.3/9.3 | 9.3/10 | 7/9.3 | 6/9.3 | 7/9 | 7/8 |
|---|---|---|---|---|---|---|---|---|---|---|
| CR1-3* | 7/9.3 | 0.98 | | | | | 0.99 | 0.01 | | |
| CR1-4 | 7/9.3 | 0.19 | | | | | 1.00 | | | |
| CR1-5 | 7/9.3 | 0.09 | | | | | 0.51 | 0.49 | | |
| JW1* | 6/9.3 | 0.02 | | | | | | 1.00 | | |
| JW2* | 6/9.3 | 0.38 | | | | | 0.01 | 0.99 | | |
| JW3* | 6/9.3 | 0.63 | | | | | 0.01 | 0.99 | | |
| JW4 | 6/9.3 | <0.01 | | | | | | 1.00 | | |
| JW5 | 6/9.3 | 0.30 | | | | | 0.01 | 0.99 | | |
| JW6 | 6/9.3 | 0.01 | | | | | | 1.00 | | |
| JW7 | 6/9.3 | 0.01 | | | | | | 1.00 | | |
| JW8 | 6/9.3 | 0.01 | | | | | | 1.00 | | |
| DW3-1* | 7/9 | 0.89 | | | | | | | 1.00 | |
| DW3-2* | 7/9 | 0.91 | | | | | | | 1.00 | |
| DW3-3* | 7/9 | 0.96 | | | | | | | 1.00 | |
| DW3-4 | 7/9 | 0.98 | | | | | | | 1.00 | |
| DW3-5 | 7/9 | 0.40 | | | | | | | 1.00 | |
| JT2-1* | 7/8 | 0.97 | | | | | | | | 1.00 |
| JT2-2* | 7/8 | 0.87 | | | | | | | | 1.00 |
| JT2-3* | 7/8 | 0.98 | | | | | | | | 1.00 |
| JT2-4 | 7/8 | 0.97 | | | | | | | | 1.00 |
| JT2-5 | 7/8 | 0.92 | | | | | | | | 1.00 |
| JT2-6 | 7/8 | 0.88 | | | | | | | | 1.00 |
| JT2-7 | 7/8 | 0.83 | | | | | | | | 1.00 |

*Samples were selected as controls

Referring again to FIG. 5, TH01 STR unsupervised clustering is shown. All pseudo-unknowns for the various TH01 STR alleles are correctly clustered and called into the respective genotypes using the unsupervised analysis feature. Clusters are highlighted by ellipsoids that represent the variance/covariance of the classified samples in a two PC dimension plot. DNA fingerprinting requires discrimination between multiple melt curves and Constellation software proved capable of discriminating even closely associated sequences and heterozygotes.

With regard to the embodiment of the inventive software described above, the software is capable of detecting, clustering and calling correctly genotypes from various HRM data sets generated using different assay conditions for both simple and complex polymorphisms. Comparisons between two different normalization techniques demonstrates that the scaling of fluorescence using a line of best fit is more appropriate to use compared to the Levenberg-Marquardt algorithm. The latter method tends to cause a loss in melt curve features that could influence the final result, post principle component extraction. For unsupervised analysis, the gap statistic proves the more appropriate method for detecting the preferred number of clusters and PC dimensionality. Therefore, these methods are preferably implemented to the work flow of the software; however, both methods are still be acceptable for the majority of possible HRM data sets.

In conclusion, the software allows the user to achieve both supervised and unsupervised genotyping of unknowns from HRM data sets in various applications of molecular biology, with the final goal being to allow for multiple run files in a diagnostic setting.

The foregoing describes preferred forms of the present invention. Modifications, obvious to those skilled in the art, can be made thereto without departing from the scope of the invention. While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below. The invention also covers all further features shown in the figures individually although they may not have been described in the afore or following description.

Furthermore, in the claims the word "comprising" does not exclude other elements or steps, and the indefinite article "a" or "an" does not exclude a plurality. A single unit may fulfil the functions of several features recited in the claims. The mere fact that certain measures are recited in mutually different dependent claims does not indicate that a combination of these measures cannot be used to advantage. Any reference signs in the claims should not be construed as limiting the scope.

We claim:

1. A computer-implemented method of analysis of melt curve data, comprising the steps of:
   (a) in a computer memory, parameter model fitting the melt curve data;
   (b) in a computer memory, performing a principal component analysis of the melt curve data; and
   (c) utilizing the principal components for clustering the melt curve data into groups.

2. The method of claim 1, wherein the melt curve data is double stranded deoxyribonucleic acid (dsDNA) melt curve data for identifying a specific sequence of dsDNA in a sample after performing a polymerase chain reaction (PCR).

3. The method of claim 1, wherein the computer memory is in a computer connected to the Internet or a network.

4. The method of claim 1, wherein the computer comprises a storage medium and a monitor or visual display device.

5. The method of claim 1, wherein the step (a) comprises fitting the melt curve data to a model of the form:

$$A + \frac{B - CT}{1 + \exp(\lambda(T - T_0))}$$

where A is an estimate of the minimum observed fluorescence; B and C are estimates of the intercept and slope of the initial part of the melt curve; $T_0$ is estimated as the point of maximum (negative) slope of the melt curve, and γ is approximately 2.

6. The method of claim 1, wherein the step (a) comprises a scaling of the melt curve to a line of best fit.

7. The method of claim 6, wherein a region of melt curve data prior to the melt curve transition and a region of melt curve data following the melt curve transition are selected and an average fluorescence value is calculated.

8. The method of claim 1, wherein at least the first two principal components are utilized in step(c).

9. The method of claim 1, wherein said clustering occurs by means of k-means clustering or hierarchical clustering.

10. The method of claim 9, wherein a gap statistic is utilized for determining the number of groups for the melt curve data.

11. The method of claim 10, wherein determining the number of groups for the melt curve data comprises the comparison of a measure of cluster quality to data known not to have any real clusters.

12. The method of claim 11, wherein the measure of cluster quality is determined applying the formula:

$$W_k = \sum_{j=1}^{k} \sum_{i \in c_j} \|x_i - \bar{x}_j\|^2$$

where $C_j$ is the j-th cluster, and $\bar{x}_j$ is its center.

13. The method of claim 12, wherein determining the number of groups for the melt curve data comprises the steps of:
   (i) clustering the observed data, varying the number of clusters k=1, 2, ..., K for a maximum K and computing $W_k$ for each k;
   (ii) generating B random reference data sets and clustering each as in step (i), computing $W_{kb}$ for k=1,2, ..., K and b=1,2, ...,B;
   (iii) computing the Gap statistic and standard error for each k applying the formulae $$\text{Gap}(k) = (1/B) \sum \log(W_{kb}) - \log(W_k)$$

and $$s_k = \sqrt{(1 + 1/B) \sqrt{\{(1/B)\sum_b (\log(W_{kb}))^2 - ((1/B)\sum_b \log(W_{kb}))^2\}}};$$

and (iv) choosing the number of clusters k to be the smallest $\hat{k}$ such that $\text{Gap}(k) \geq \text{Gap}(k+1) - s_{k+1}$.

14. The method of claim 1, wherein a Bayes Information Criterion analysis is utilized for determining the number of groups for the melt curve data.

15. The method of claim 1, wherein said melt curve data is for a known substance and said clustering utilises linear discriminant analysis to cluster the melt curve data into groups.

16. The method of claim 1, wherein said clustering utilises a typicality index to assign the melt curve data into a group.

17. The method of claim 1, wherein said melt curve and said clustering utilize posterior class probabilities to cluster the melt curve data into groups.

18. A computer-implemented system for analysis of melt curve data, comprising a non-transitory computer readable medium comprising:
   import means to import raw high resolution melting data;
   parsing means to syntactically analyze the imported data; and
   cropping means to allow a user to avoid regions of non-specific amplification products.

19. The system of claim 18, further comprising sample selection means to allow a user to select a sample, and mode selection means to allow a user to select between analysing a supervised data set or an unsupervised data set following the sample selection.

20. The system of claim 19, further comprising parameter selection means to select a most appropriate cluster number and a most appropriate principal component number via k-means clustering, Gap statistics, or both, when the user selects analysing an unsupervised data set.

21. The system of claim 20, further comprising control selection means to allow the user to select the appropriate controls for each genotype when the user selects analysing a supervised data set, wherein linear discriminant analysis is used and the appropriate number of principal components is determined via a cross-validation function if more than two controls are used for each group and wherein nearest neighbor classification of samples into groups which is proceeded by a re-computation using linear discriminant analysis is used if one single control activates.

22. A method of analysis of melt curve data, comprising the steps of:
   (a) generating melt curve data with a thermal cycler;
   (b) storing the melt curve data in an electronic file on a computer;
   (a) in a computer memory, parameter model fitting the melt curve data;
   (b) in a computer memory, performing a principal component analysis of the melt curve data; and
   (c) utilizing the principal components for clustering the melt curve data into groups.

* * * * *